United States Patent
Hirsh (10) Patent No.: US 7,931,594 B2
(45) Date of Patent: Apr. 26, 2011

(54) REGIONAL ANESTHETIC METHOD AND APPARATUS

(75) Inventor: Robert A. Hirsh, Merion Station, PA (US)

(73) Assignee: The Cooper Health System, Camden, NJ (US)

(*) Notice: Subject to any disclaimer, the term of this patent is extended or adjusted under 35 U.S.C. 154(b) by 324 days.

(21) Appl. No.: 11/555,965

(22) Filed: Nov. 2, 2006

(65) Prior Publication Data

US 2007/0129628 A1  Jun. 7, 2007

Related U.S. Application Data

(63) Continuation-in-part of application No. 11/292,681, filed on Dec. 2, 2005.

(51) Int. Cl.
*A61B 8/14* (2006.01)

(52) U.S. Cl. ........ 600/454; 600/437; 600/449; 600/463; 604/264

(58) Field of Classification Search .......... 600/437–467, 600/471; 604/264
See application file for complete search history.

(56) References Cited

U.S. PATENT DOCUMENTS

| | | | |
|---|---|---|---|
| 4,808,157 A | 2/1989 | Coombs | |
| 4,887,606 A * | 12/1989 | Yock et al. | 600/461 |
| 5,090,414 A * | 2/1992 | Takano | 600/461 |
| 5,150,714 A * | 9/1992 | Green | 600/442 |
| 5,156,596 A * | 10/1992 | Balbierz et al. | 604/164.11 |
| 5,259,385 A * | 11/1993 | Miller et al. | 600/453 |
| 5,480,421 A | 1/1996 | Otten | |
| 5,484,416 A * | 1/1996 | Gittings | 604/164.08 |
| 5,651,364 A * | 7/1997 | Yock | 600/439 |
| 5,685,852 A * | 11/1997 | Turkel et al. | 604/159 |
| 5,779,642 A * | 7/1998 | Nightengale | 600/461 |
| 5,779,643 A * | 7/1998 | Lum et al. | 600/462 |
| 5,902,245 A * | 5/1999 | Yock | 600/463 |
| 5,972,012 A | 10/1999 | Ream et al. | |
| 6,221,015 B1 * | 4/2001 | Yock | 600/439 |
| 6,409,673 B2 * | 6/2002 | Yock | 600/463 |
| 6,572,554 B2 * | 6/2003 | Yock | 600/463 |
| 6,679,899 B2 | 1/2004 | Wiener et al. | |
| 6,764,450 B2 * | 7/2004 | Yock | 600/466 |
| 6,795,737 B2 | 9/2004 | Gielen et al. | |
| 6,981,947 B2 | 1/2006 | Melker | |
| 7,131,948 B2 * | 11/2006 | Yock | 600/466 |
| 7,263,888 B2 * | 9/2007 | Barshinger et al. | 73/606 |
| 7,328,064 B2 * | 2/2008 | Mathiesen et al. | 604/21 |
| 7,555,343 B2 * | 6/2009 | Bleich | 607/43 |
| 2001/0051766 A1 | 12/2001 | Gazdzinski | |
| 2003/0236489 A1 | 12/2003 | Jacobson et al. | |
| 2005/0033551 A1 | 2/2005 | Takai et al. | |
| 2005/0081636 A1 * | 4/2005 | Barshinger et al. | 73/606 |

\* cited by examiner

*Primary Examiner* — Long Le
*Assistant Examiner* — Sanjay Cattungal
(74) *Attorney, Agent, or Firm* — Michael B. Fein; Cozen O'Connor (57) ABSTRACT

A system and method for regional anesthesia using ultrasound to assist in locating the anesthetic needle are disclosed. One or more piezo-electric crystal transducers is placed either at the tip of the needle or near the tip of the needle on a stylet which is inserted into the lumen of the needle. The transducer(s) are pulsed with ultrasonic frequency, the reflected ultrasonic signals from structures are detected and converted into a digital signal and may be displayed in an oscilloscopic format to indicate anatomical structures forward to the needle and allow the medical professional to avoid errors and/or increase efficiency and accuracy. An array of transducers can be pulsed in a phased array fashion to generate a 2D image, or a single transducer can be pulsed to generate a 1D image. A 2D image can also be obtained by mechanically sweeping a single transducer, for example by means of a miniature motor in or at the base of a needle or stylet.

19 Claims, 6 Drawing Sheets

REGIONAL ANESTHETIC METHOD AND APPARATUS

CROSS-REFERENCE TO RELATED APPLICATIONS

This is continuation-in-part of Ser. No. 11/292,681, filed Dec. 2, 2005, for which benefit is claimed and which is incorporated by reference.

FIELD OF THE INVENTION

This invention relates generally to the field of regional anesthesia, epidural needles and methods of placement of epidural needles and other regional anesthesia needles.

BACKGROUND OF THE INVENTION

Regional anesthesia involves the introduction of local anesthetics, with the intention of blocking the nerve supply to a specific part of the body so the patient cannot feel pain in that area when a surgical operation is performed, for pain relief during onset of labor or during labor, or for chronic pain. Regional anesthesia is used in both epidural and subdural or spinal procedures, and can involve plexus blocks and blocks of peripheral nerves.

Epidural anesthesia, one form of regional anesthesia, has gained popularity over the years as being an effective manner of blocking pain without requiring entry to the dura mater of the spinal cord (i.e., a spinal anesthesia). In fact, epidural anesthesia is often the anesthesia of choice in child birth. The surgical procedure for epidural anesthesia typically starts with the utilization of a 17- or 18-gauge Touhy needle in the lumbar region in order to puncture the skin, and to traverse at least the supraspinous ligament. The Touhy needle is basically a hollow needle having an angled distal tip which is slightly curved (i.e., a Huber point) and a proximal luer fitting, and a solid stylet which sits inside and substantially fills the hollow needle. Once the skin and supraspinous ligament have been traversed by the Touhy needle, the solid stylet is removed from within the hollow needle, and an air filled syringe is coupled to the proximal luer fitting of the hollow needle. With pressure being applied to the plunger of the syringe as well as to the barrel of the syringe, the hollow needle of the Touhy needle is slowly advanced past the interspinous ligament and ligamentum flavum until the needle enters the epidural space between the ligamentum flavum and the dura mater of the spine. Location of the epidural space which is filled with connective tissue, fatty tissue, and blood vessels is indicated by loss of resistance; i.e., less resistance to the injection of air through the needle. In other words, when the pressure applied by the practitioner to the plunger causes the plunger to readily push air through the needle, the practitioner can assume that the epidural space has been reached. Upon entry to the epidural space, the syringe is carefully disconnected from the hollow needle (extreme care being taken to keep the needle in its exact position), and a catheter is threaded through the hollow needle. Because the hollow needle has an angled distal end, upon reaching the distal end of the hollow needle, the catheter is directed into the epidural space which is substantially perpendicular to the direction of the needle. The catheter is advanced only two to three centimeters into the epidural space in order to reduce the likelihood that it might exit though an intervertebral foramen, with resulting inadequate epidural anesthesia. With the catheter in place, a test dose, repeated injections, or a continuous flow of anesthesia may be administered through the catheter.

A conventional method of placing regional anesthetic needles is to use anatomical landmarks, tapping on the barrel of an attached syringe to feel the way forward until a loss of resistance is obtained. Because the person placing the needle must rely on tactile information, there is a risk of errors such as dural punctures or "wet taps" during lumbar epidurals and spinal chord injury during cervical or thoracic epidural placements.

While the apparatus and methods for administering regional anesthesia have proved successful over a long period of time, there are drawbacks to those approaches and methods. With regard to the Touhy needle in particular, although it is provided with a curved Huber point, the Touhy needle is still sharp. Use of the Touhy needle therefore runs the risk that the practitioner, i.e., physician, operator, or other person trained to perform this procedure, might overshoot the epidural space and enter the subdural space between the dura mater and the arachnoid mater of the spine, or the subarachnoid space. Such a mistake could result in extreme over-application of anesthesia with a possible high level of spinal anesthesia, necessitating endotracheal intubation of the trachea and mechanical ventilation of the patient. Similar complications could also occur during the disconnection of the syringe from the Touhy needle and insertion of the catheter, as the patient might move, or the needle might not be held properly in position. Such movement of the needle could result in the undesirable entry of the needle and/or catheter into the subdural or subarachnoid spaces.

In order to obtain better information during regional anesthesia needle placement, it has been proposed to use X-ray fluoroscopic techniques to place the needles, but in many cases it is not possible to use X-ray, for example in the case of pregnant women or at the bedside in the trauma intensive care unit (TICU).

Recently it has been proposed to use 2-D echo to facilitate placement of regional anesthetic needles. MicroMaxx™ hand-held ultrasonic devices, manufactured by SonoSite, Inc., which use 2D ultrasound on the patient's skin, have been used at Dartmouth-Hitchcock Medical Center to assist in proper placement of the needle. The use of a 2D echo device is complicated by the need for the use of an acoustic gel, which can compromise sterility when used to assist with regional anesthetic needle placement. Moreover, the 2D echo device is not useful for imaging structures inside the bony spinal canal because the structure of bone tissue scatters ultrasound randomly, such that no intelligible image can be obtained from sound reflected from tissue structures that are deep to bone.

Accordingly there exists a long-felt and continuing need for apparatus and methods for placement of epidural needles and other regional anesthesia needles.

SUMMARY OF THE INVENTION

It is therefore an object of this invention to provide apparatus and methods for safer and easier regional anesthesia. It is another object of the invention to provide apparatus for use in a guided method of placing needles for regional anesthesia which do not suffer from the disadvantages of currently used techniques and apparatus.

It is also an object to provide an improved epidural needle system and an improved method for epidural injections which provides better anatomical information than mere tactile information.

These objects and others which will become apparent from the following disclosure and drawings are achieved by the present invention which in some aspects comprise a system for regional anesthesia comprising (A) a needle having a lumen, a length, and a tip, (B) an optional stylet having a length and a tip, the stylet adapted to be inserted into the lumen of the needle, (C) a piezo-electric transducer means, (D) means for pulsing the transducer with ultrasonic frequency, (E) means for detecting reflected ultrasonic signals from structures; and (F) means to convert the reflected ultrasonic signals into a digital signal; and (G) means to display the digital signal; the transducer means located either at the tip of the needle or at the tip of the optional stylet.

In some aspects the invention comprises a method of placing a regional anesthetic needle comprising providing a piezo-electric crystal located at or near the tip of the needle, pulsing the transducer with ultrasonic frequency, detecting reflected ultrasonic signals from structures deep to the tip of the needle; converting the reflected ultrasonic signals into a digital signal representing anatomical information forward to the needle; displaying the digital signal, and guiding the needle to a desired location while preventing the needle from touching an undesired location. "Deep to the tip" and "forward to the needle" are used interchangeably to refer to the anatomy of the patient distal to the tip of the needle as it is being placed. "Desired location" refers to the placement of the needle in a safe and proper anatomical area.

Suitable regional needles have a distal end and a proximal end, with the distal end terminating in an aperture and having a tip adapted for insertion through tissue into a nerve sheath of a patient, and with the proximal end being adapted for fluid connection. In the case of Touhy needles which are typically used for epidural anesthetics, the tip on the distal end has a beveled aperture.

In some embodiments the system comprises a stylet. Stylets are conventionally used when regional anesthetic needles are placed, and any of the conventional stylets can be used with the system of the invention, or a special stylet with one or more piezo-electric transducer(s) on the tip can be used. Such stylets are disclosed in Gutting, U.S. Pat. No. 5,484,416, and in Yock, et al., U.S. Pat. No. 4,887,606, each of which is incorporated by reference in its entirety. Electrical wires can be provided through the stylet to connect the transducer(s) to the opposite end of the stylet when they are present at the tip of a stylet used in the present invention, as shown in Yock, et al., so that the ultrasound signal can be sent to and received from the transducer(s).

Suitable transducers include but are not limited to small piezo-electric crystals which are commercially available, for example a 20 MHz PZTSA transducer having a 1 mm diameter. In some embodiments, a single transducer is used. In some embodiments, an array of transducers comprising at least two transducers, is used. The transducer or transducers can be bonded to the stylet or tip of the needle itself with any means, including, for example, an adhesive such as Emerson IG0101 microballoons in epoxy. Electrical conductive material can be used in addition to the wires, or instead of one conductor, for example Trabond 2902 silver epoxy is suitable for this purpose. In some embodiments the transducer or transducers are encapsulated in a sleeve, for example a polyimide or other plastic sleeve. Suitable wiring systems are used to connect such arrays to the ultrasound signal generation and reception system, and suitable electronics and software may be used to convert the signal to a displayed graph which can be interpreted by the medical professional and used to guide the placement of the needle.

When one transducer is used, a 1D graphical representation of amplitude with respect to time can be displayed for the benefit of the operator. "Operator" as used herein refers to a physician, other trained professional, student or other trainee.

By looking at the signal from the acoustic interface between dura matter and cerebrospinal fluid (CSF), the operator can judge distance between the needle tip and dura, and thereby avoid puncturing the dura.

When two or more transducers are used in an array, a 2D image of tissues distal to the needle can be displayed by activating the transducers in a phased array fashion to sweep the beam radially from the point of the needle with appropriate controller and software. Because the needle is close to the structure, and since attenuation increases with frequency and distance, in some embodiments it is possible to use much higher frequencies than conventionally used. Although 1D images are useful to assist with placing needles used for regional anesthetics, 2D images distal to the needle allow the operator to see cross sections of the spinal cord, nerve roots, and cauda equina, for example.

Means for pulsing suitable for use in the present invention include conventional signal generators and power supplies capable of generating an ultrasound signal at the transducer. Conventional electronics may be used to receive the reflected ultrasound signals and convert analog to digital signals. Conventional programmed microprocessors may be used to convert the reflected ultrasound signals to, for example, a simulation of an oscilloscope displayed on a computer display, for example on a laptop computer or other computer suitable for an operating room environment.

The regional anesthetic needle system of the invention uses the transducer means at the tip of the needle or the stylet to obtain an ultrasound image of the anatomy of the patient distal to the needle, to gauge depth, and thereby assist with the accurate and safe placement of the regional anesthetic needle.

In addition to the ultrasound imagery, the system in some embodiments includes means, such as controller programming and a signal module, to generate an audible signal indicating the distance between the tip of the needle and the tissues distal to the tip. In such embodiments, the operator can use the audible signal to assist in placing the needle. In some embodiments the system can increase the number of sounds or pitch as the tip gets closer to tissue structure.

In some embodiments of the invention, a sweeping transducer is provided at the distal end of the Touhy needle, with wiring leading to an ultrasound generator and receiver. The transducer can be swept in a see-saw manner by any of a number of means, for example by providing a reciprocating vertical strut and means to reciprocate the strut such as, for example, a MEMS motor at the proximal end of the reciprocating strut. The transducer can be supported by various arrangements, for example a stage which has two sides, and by using a hinge arrangement to attach the reciprocating vertical strut to one side, and a hinge arrangement to attach a stationary vertical strut to the other side. Alternatively, two reciprocating struts can be provided, each hingedly attached to the stage supporting the transducer, and means to reciprocate the two struts in opposite directions to cause the transducer to reciprocate in a see saw fashion.

In the embodiments with two struts, they can have D-shaped cross-sections with flat sides facing each other, or they can have fluted D-shapes to provide passageways between the round portion, when viewed in cross-section, for fluid. When fluted D-shaped cross-sections are provided, there are still flat sides facing each other in certain embodiments. Alternatively, the struts can be separated and not be D-shaped and not be touching each other. A vertical channel can be provided in one of the struts, for example the stationary strut in embodiments which include such a stationary strut, and wires can be provided in such channel.

BRIEF DESCRIPTION OF THE DRAWINGS

Certain embodiments of the invention are illustrated in the drawings and will be described in more detail below with reference thereto. The illustrated embodiments are only examples of the invention and the description thereof is not intended to imply a limitation on the invention. The invention is capable of considerable modification, alteration and equivalents in form and function.

DESCRIPTION OF THE INVENTION

Figure 1:
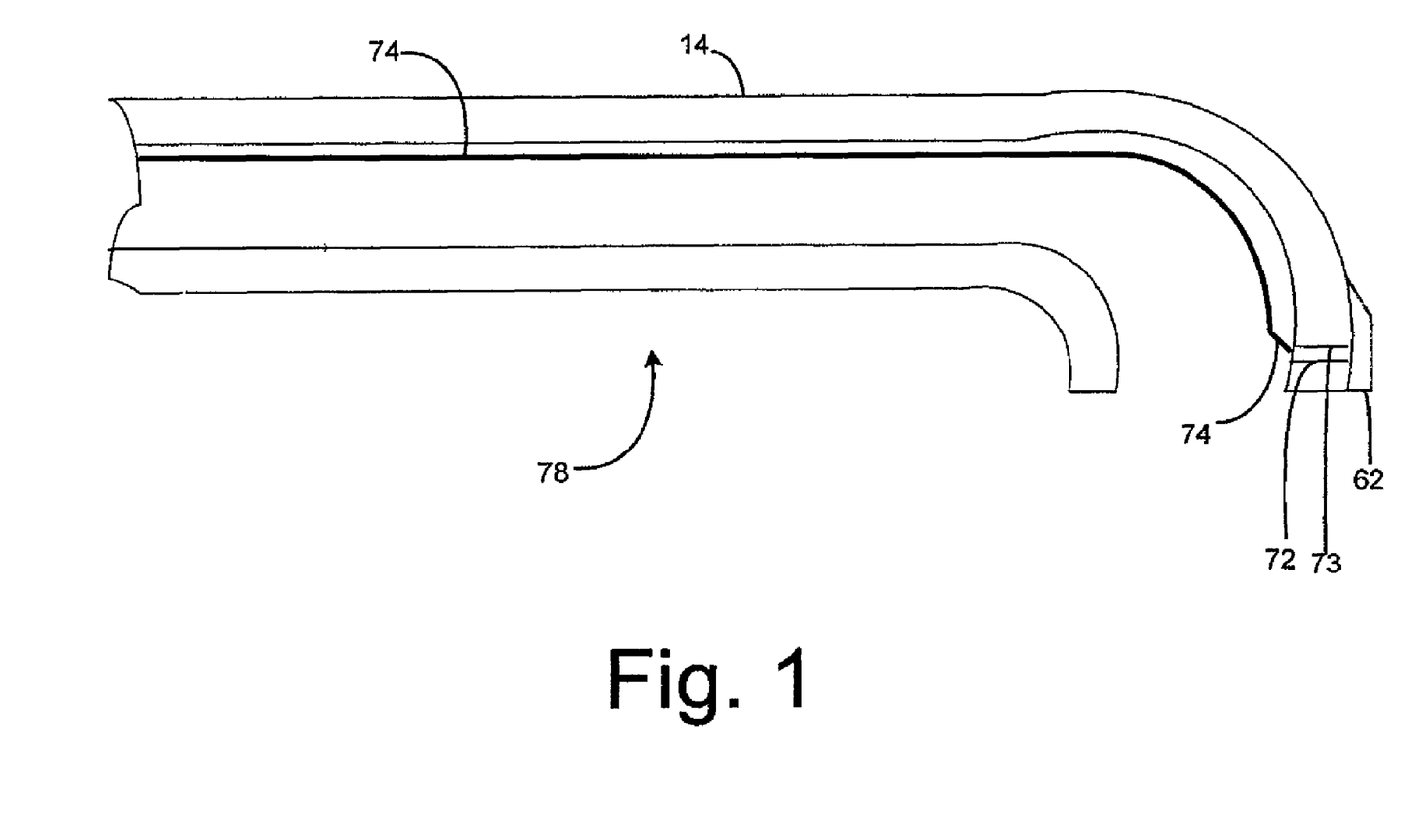
FIG. 1 is a partial cross-sectional view of a Touhy needle having a transducer at the distal end.

FIG. 1 shows an embodiment of a regional anesthetic needle 78 according to the invention wherein a conventional Touhy needle 14 is modified by providing a piezo-electric crystal 62 on the distal portion of the needle, connected by wires 72, 73 through the front of the needle, and the wire 74 continuing through the lumen of the needle. The wire 74 can be adhered to the inside wall forming the lumen. In some embodiments conductive material is used rather than wire, for example conductive polymers can be adhered to the inside wall of the lumen.

Figure 2:
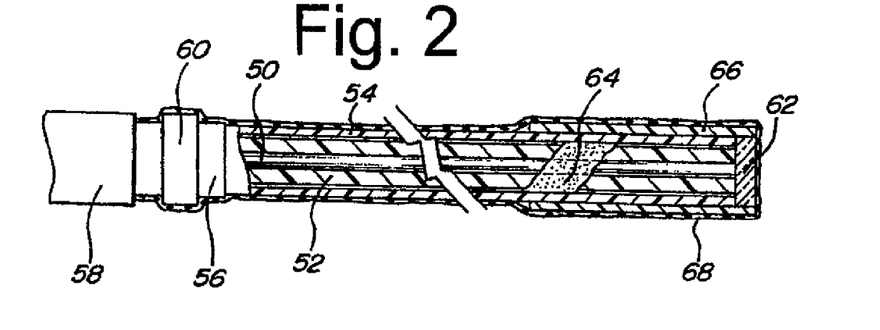
FIG. 2 is a partial cross-sectional view of a stylet having a transducer at the distal end.

FIG. 2 shows an embodiment of stylet 16 having a transducer 62 at the distal end. A solid center conductor 50 is surrounded by a dielectric tube 52. The conductor in this embodiment is surrounded by a Teflon dielectric tube, which provides improved noise suppression during operation. Conductor 50 can be composed of copper, silver, or silver-plated copper. A conductive adhesive 54 is coextruded over dielectric tube 52 which is a thin layer of nylon, capable of being adhered to by conductive adhesive. Shielding means 56 covers a portion of dielectric tube 52. Shielding means 56 is a braid or a foil wrap over a drain wire. A silicon, Teflon or other type of jacket 58 completes a portion of the probe-cable assembly. Jacket 58 and shielding means 56 are preferably stripped off the dielectric tube 52, leaving about ¼ of an inch of the shielding means exposed. Anchoring means 60 anchors shielding means 56 to dielectric tube 52. Anchoring means 60 can be a conductive ring or hollow cylindrical crimp. The exposed length of dielectric tube 52 extending beyond shielding means 56 can be any preselected length necessary, depending on the maximum length of needle with which the probe is intended for use.

Figure 3:
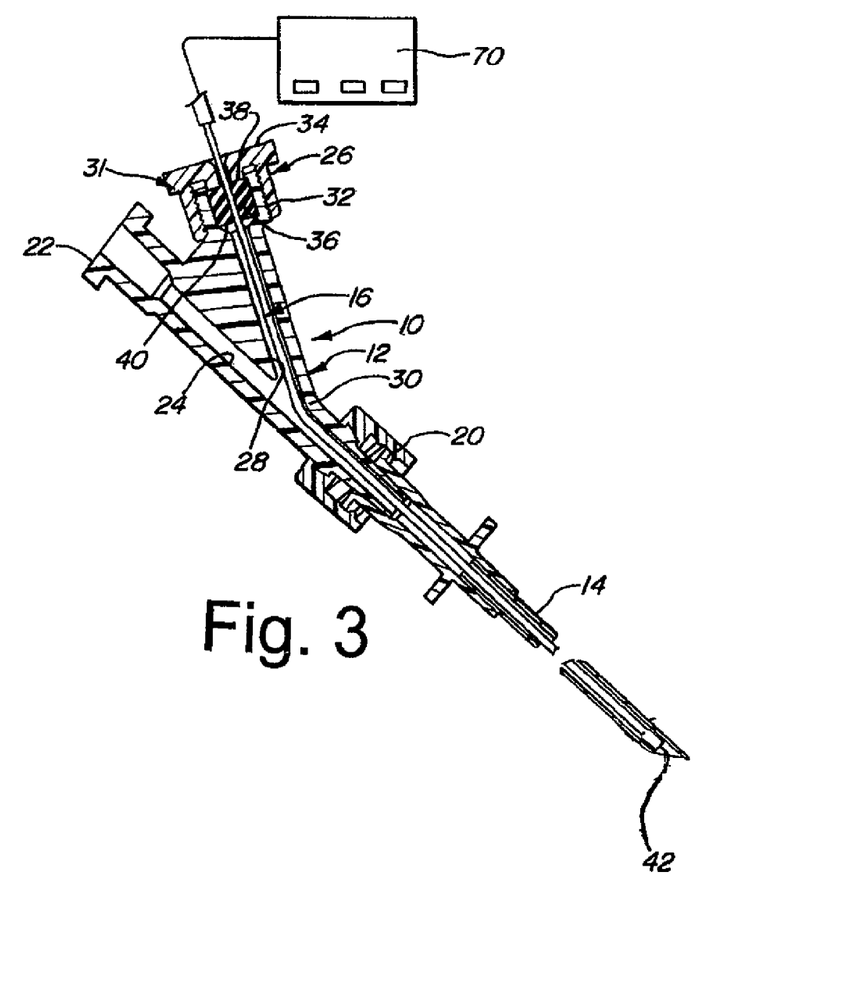
FIG. 3 is a partial cross-sectional view of a regional anesthetic needle and stylet assembly.

FIG. 3 illustrates needle assembly 10 including housing 12, needle 14 and stylet 16. Housing 12 includes first end 20 adapted to be connected to a variety of needles. Second end 22 is axially opposite first end 20 and preferably coaxial with first end 20. Second end 22 is adapted to be connected to a syringe, for example. Housing 12 includes first channel 24 defined between first end 20 and second end 22. Third end 26 is adapted to receive stylet 16. A second channel 28 is defined between third end 26 and a medial location along first channel 24 that defines a bend 30. As illustrated, when in use, stylet 16 is axially movable through second channel 28 and a portion of first channel 24 and needle 14 such that stylet 16 bends around bend 30. First channel 24 and second channel 28 typically have a relative angle of orientation of approximately 30 degrees.

Third end 26 preferably includes locking means 31. Locking means 31 includes external threads 32 which can be formed on third end 26 of housing 12. Internally threaded adjustable member 34 is received over external threads 32. Pressure means 36 is contacted by surface 38 on adjustable member 34. Pressure means 36 is received in the portion of housing 12 indicated at 40 such that the relative adjustment of member 34 along external threads 32 causes surface 38 to bear against and apply an axial pressure on pressure means 36. Such axial pressure compresses pressure means 36 in such manner that pressure means 36 exerts a radially compressive force on stylet 16. In this manner, stylet 16 is temporarily held axially fixed relative to housing 12. Pressure means 36 also acts as a seal against leakage from the third end 26.

Figure 4:
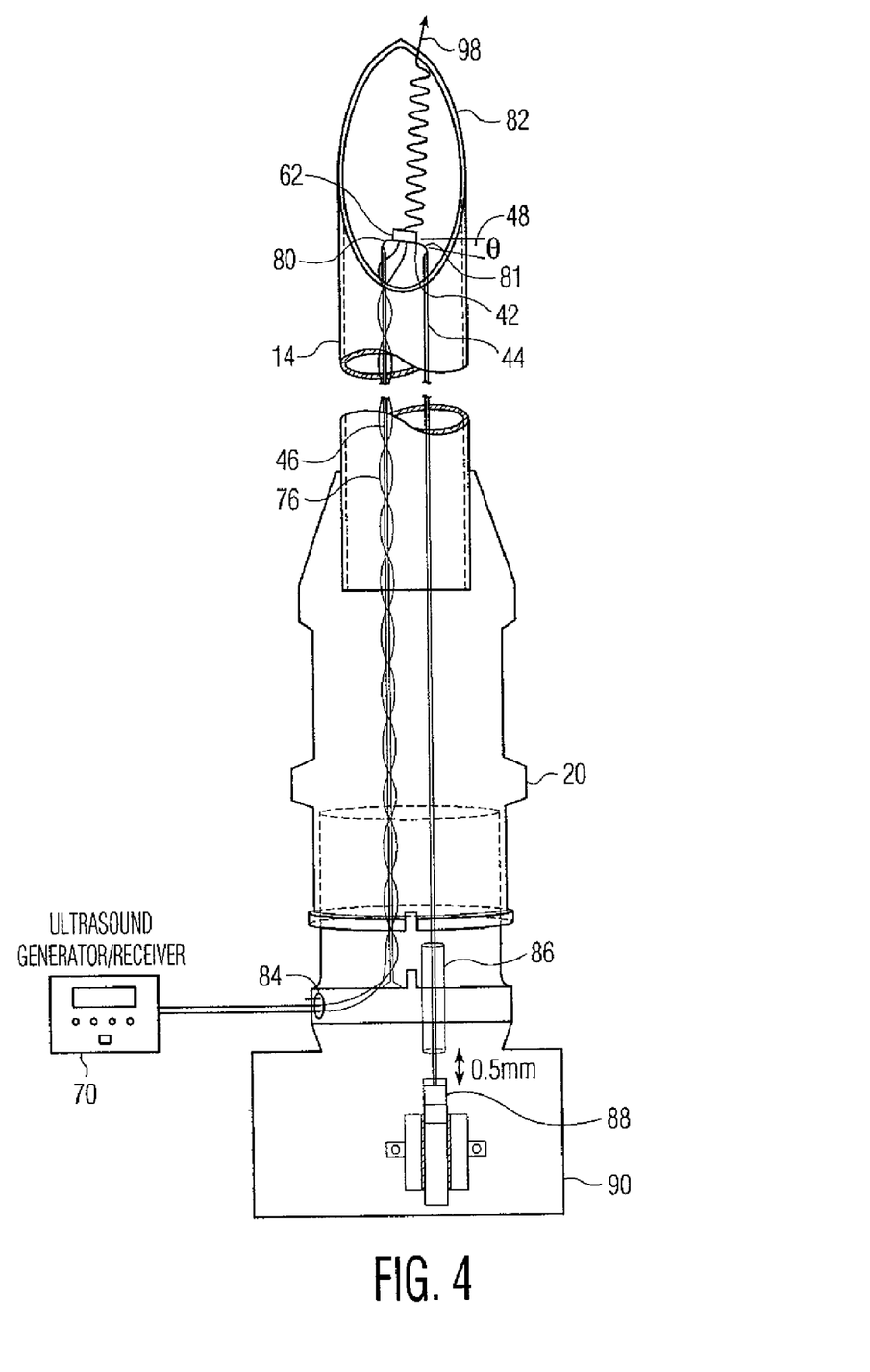
FIG. 4 is a partial cross-sectional view of a Touhy needle having a sweeping transducer at the distal end, with wiring leading to an ultrasound generator and receiver.

FIG. 4 shows an embodiment which includes a modified system including a Tuohy needle 14 for providing two dimensional ultrasound imaging of areas distal to the Touhy needle 14. In this embodiment, the transducer 62 is mounted on a see-sawing stage 42 which is bonded on one side 80 to a stationary vertical strut 46 and on the opposite side 81 is bonded to a reciprocating vertical strut 44 driven by a MEMS motor 88 in a motor housing 90 which causes the reciprocating vertical strut 44 to travel back and forth in a vertical, or proximal-distal, direction and thereby cause the direction of ultrasound 98 to sweep horizontally between right and left, or across the vertical axis through the opening in the tip 82 of Tuohy needle 14. The stage moves between angle ø 48 and negative angle ø off horizontal. Transducer 62 is electrically connected to ultrasound generator/receiver 70 via electrical wires 76 wrapped around stationary vertical strut 46 and exiting the base 20 of the needle at exit hole 84. A tunnel 86 for the reciprocating vertical strut 44 is provided at the base of the needle housing first end 20 to provide guidance for strut 44.

Figure 5:
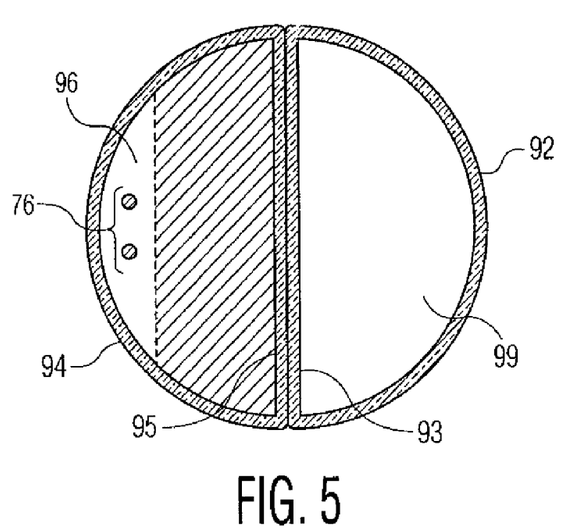
FIG. 5 is a cross-sectional view of an embodiment of a stationary vertical strut and a reciprocating vertical strut, with their flat sides facing each other.

FIG. 5 shows cross-sections of a first embodiment of the struts where reciprocating strut 92 and stationary strut 94 are each D-shaped, with the flat parts 93 and 95, respectively, facing each other. Reciprocating strut 92 is solid 99 in this embodiment, and stationary strut 94 has a channel 96 through which wires 76 are threaded rather than being wrapped around the stationary strut 46 of FIG. 4.

Figure 5A:
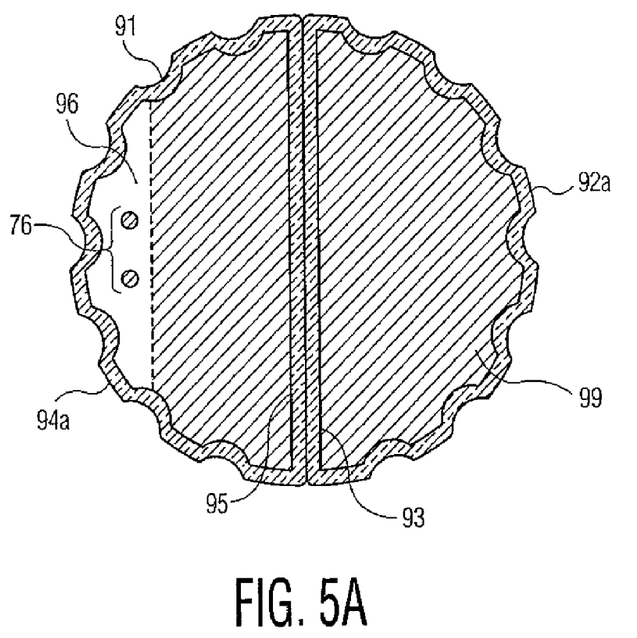
FIG. 5A is a second embodiment of a stationary vertical strut and a reciprocating vertical strut, with their flat sides facing each other, including fluting in the curved sides of the struts.

FIG. 5A shows cross-sections of a second embodiment of the struts where reciprocating strut 92a and stationary strut 94a are each generally D-shaped, with the flat parts 93 and 95, respectively, facing each other. The struts in this embodiment are fluted 91 (shown as indentations in cross-section) so as to provide fluid passageways between the struts 92a, 94a, and the internal wall of needle 14, shown in FIG. 4.

Figure 6:
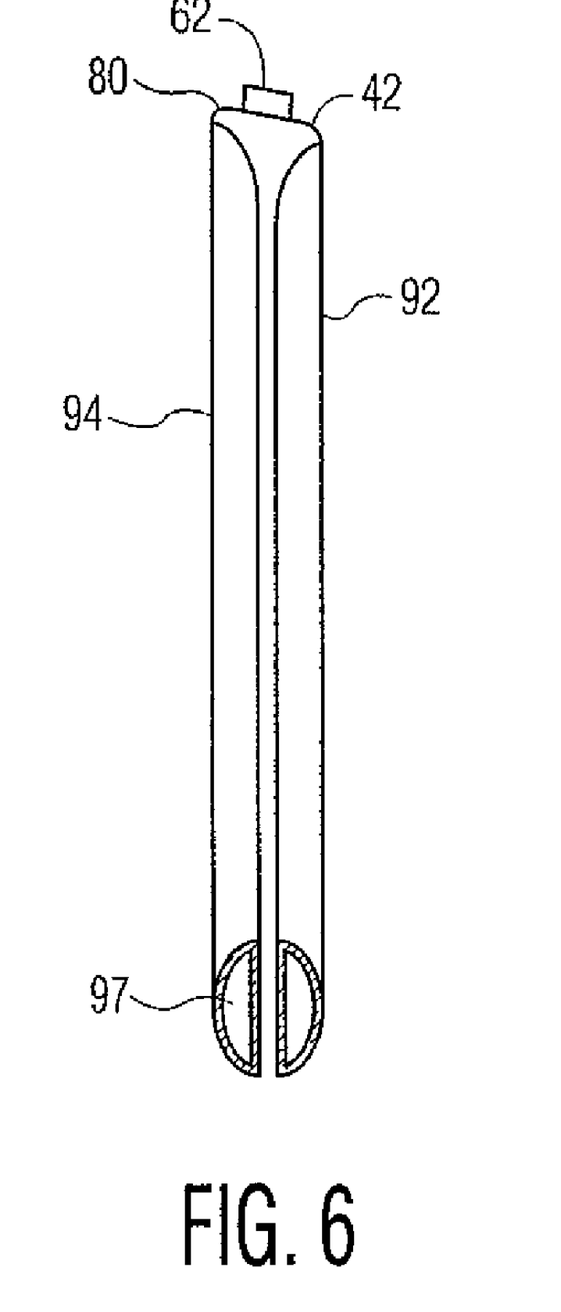
FIG. 6 is an elevational view partly in cross-section of the struts embodiment of FIG. 5 with a transducer mounted on stage which extends between the outer portions of the distal ends of the struts.

FIG. 6 illustrates and embodiment similar to that of FIG. 5 except that struts 92 and 94 are each hollow 97. In this view, stage 42 supporting transducer 62 is bonded at 80 to the outer sides of struts 92 and 94. When the reciprocating strut 92 is driven by the motor as illustrated in FIG. 4, the stage see saws back and forth, causing the path of the ultrasound to sweep and thereby enable two dimensional imaging.

Figure 7:
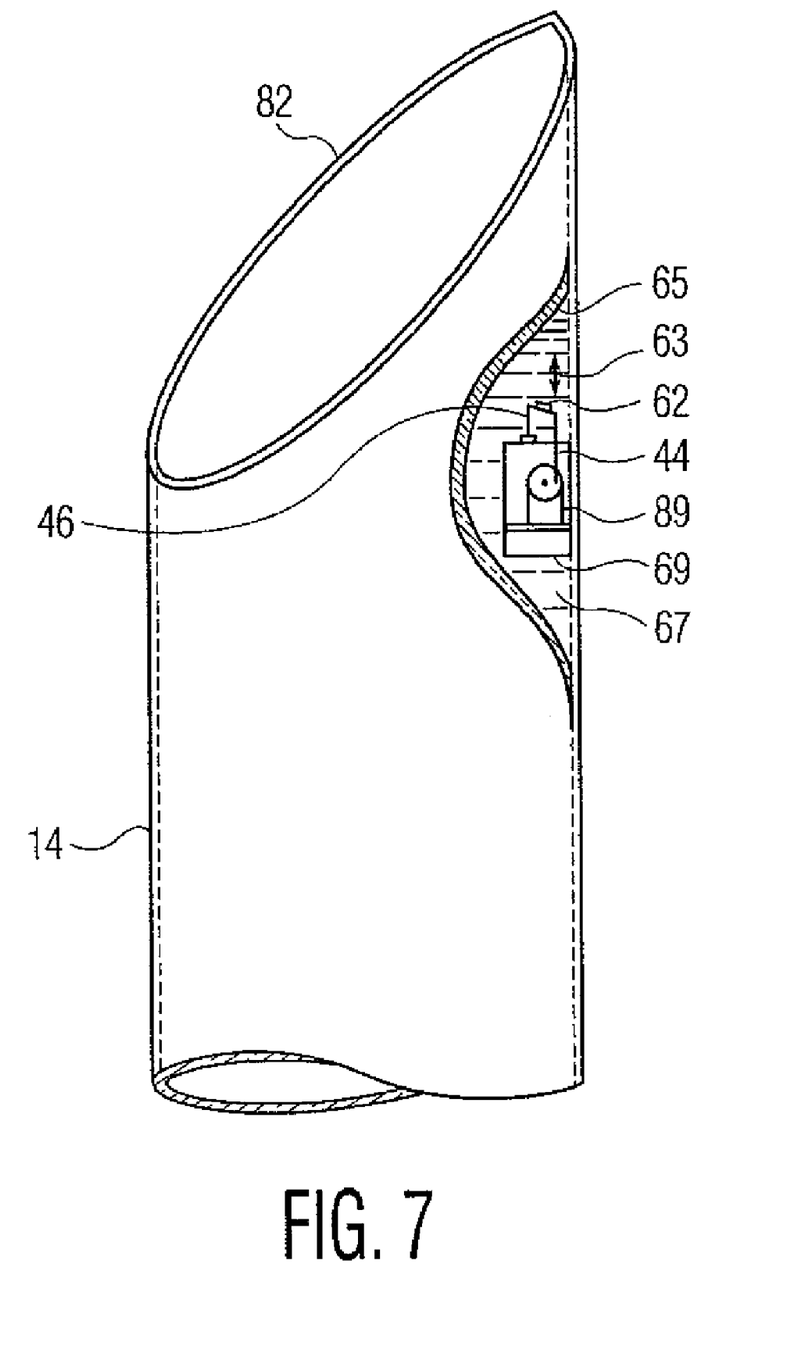
FIG. 7 is an elevational view of the tip portion of an embodiment of a Tuohy needle with a MEMS motor mounted in a dome-shaped housing filled with acoustic conductive fluid or gel which is an electrical insulator.

FIG. 7 illustrates a different embodiment of Tuohy needle 14 wherein a MEMS motor 89 is mounted on a base 69 within a dome-shaped housing 65 near the tip 82 of the needle 14. The dome shaped housing 65 is filled with acoustic conducting fluid or gel 67. The motor causes reciprocating strut 44 to move in the direction indicated by arrows 63 to cause transducer 62 stage 42 to see saw while stationary strut 46 maintains one side of stage 42 to remain stationary.

A novel system and method for regional anesthesia using ultrasound to assist in locating the anesthetic needle has been described. One or more piezo-electric crystals are placed either at the tip of the needle or near the tip of the needle on a stylet which is inserted into the lumen of the needle. The ultrasound signal from the transducer is keyed or pulsed with ultrasonic frequency, the reflected ultrasonic signals from structures are detected and converted into a digital signal and displayed for the operator to indicate anatomical structures forward, i.e., distal, to the needle and allow the operator to avoid errors. The display may be in an oscilloscopic format.

As a further improvement to regional anesthesia systems and methods for locating anesthetic needles using ultrasound, the needle or the stylet can include means for sweeping the transducer means and corresponding means for controlling the sweeping and processing the ultrasound signals into a two dimensional image showing the anatomical configuration just distal to the tip of the needle and thereby guiding the person in locating the needle properly and safely.

In addition to the sweep means illustrated in the drawings wherein a horizontal hinged member has a first end and a second end supporting the transducer means and a stationary vertical member is hinged to the first end and a reciprocating vertical member is hinged to the second end, the transducer member being supported on the horizontal hinged member, two reciprocating members can be provided in order to cause a horizontal member to see saw, or the horizontal member can be eliminated in favor of a transducer which spans the full distance between the support members. Many other embodiments are possible, as long as they result in a sweeping of the ultrasound generator and receiver of reflected ultrasound and result in a two dimensional view of the anatomy.

The linear motor can be a MEMS motor, or can be any micromotor means which is now or later becomes available. The micromotor art is developing and becoming more miniaturized, and in some embodiments the most miniature motor possible is most desirable.

It may also be possible in the future for a two dimensional image to be possible by merely electronic means rather than physically reciprocating the transducer means. For example a lens which is controllable by software can be provided distally to the transducer so that the direction of the ultrasound signal can be modified without physically moving the transducer.

While the invention has been described and illustrated in sufficient detail that those skilled in this art can readily make and use it, various alternatives, modifications, and improvements should become readily apparent without departing from the spirit and scope of the invention. All cited references are hereby incorporated by reference.

What is claimed is:

1. A system comprising (A) a regional anesthetic needle having a lumen, a length, and an angled distal tip which is slightly curved, (B) a solid stylet having a length approximately equal to that of the lumen and a tip, the stylet, adapted to be when inserted into the lumen of the needle, substantially fills the lumen, (C) an ultrasound transducer located at the tip of the stylet, (D) means for keying an acoustic wave from the ultrasound transducer, (E) means for detecting reflected acoustic wave from structures comprised of dura matter; and (F) a microprocessor programmed to convert the reflected acoustic waves into a digital signal representing distance from distal end of needle to dura matter; and (G) means to display the digital signal; the system configured so that when the stylet is inserted into the lumen of the needle, the ultrasound transducer is aligned with the tip of the needle, and the system configured to assist a user to avoid contact with the dura matter by determining the depth of the distal end of the regional anesthetic needle relative to the dura matter during placement of the regional anesthetic needle.

2. The system of claim 1 further including means to sweep the ultrasound transducer.

3. The system of claim 1 further including a horizontal hinged member having a first end and a second end supporting the ultrasound transducer, a stationary vertical member hinged to the first end of the horizontal hinged member and a reciprocating vertical member hinged to the second end of the horizontal member, a linear motor coupled to the reciprocating vertical member, wherein the ultrasound transducer is supported on the horizontal hinged member.

4. The system of claim 1 further including a horizontal hinged rigid stage having a first end and a second end supporting a ultrasound transducer, a vertical member hinged to the first end and a vertical member hinged to the second end, a linear motor coupled to one or both of the vertical members and adapted to cause the rigid stage to reciprocate and thereby sweep the ultrasound transducer.

5. The system of claim 1 further including means to sweep the direction of the ultrasound from the ultrasound transducer without physically moving the ultrasound transducer so as to generate a two dimensional image from the reflected ultrasound.

6. The system of claim 1 wherein the ultrasound transducer means comprises one piezo-electric crystal.

7. The system of claim 1 wherein the ultrasound transducer means comprises at least two piezo-electric ultrasound transducers in an array.

8. The system of claim 1 wherein the means for pulsing the ultrasound transducer comprises a signal generator electrically connected to the ultrasound transducer.

9. The system of claim 1 wherein the means (G) for displaying the signal comprises a computer programmed to display a representation or simulation of an oscilloscope.

10. The system of claim 1 wherein the needle is a Touhy-type needle.

11. The system of claim 1 wherein the ultrasound transducer comprises an array of ultrasound transducers and the means for keying an ultrasound signal from the ultrasound transducer comprises a controller programmed to activate the ultrasound transducers in a phased fashion to sweep a beam radially from the point of the needle so as to generate a two dimensional (2D) image of dura matter distal to the needle.

12. The system of claim 1 further including means to generate an audible signal indicating the distance between the tip of the needle and dura matter distal to the tip.

13. The system of claim 1 further including means to generate an audible signal indicating the distance between the tip of the needle and dura matter distal to the tip, wherein the number of sounds increases as the tip gets closer to dura matter structure.

14. The system of claim 1 further including means to see-saw the ultrasound transducer and means to process acoustic signals from the ultrasound transducer to provide two dimensional imaging.

15. The system of claim 14 wherein the means to see-saw the ultrasound transducer comprises a see-sawing stage upon which the ultrasound transducer is mounted, a reciprocating vertical strut bonded to one side of the stage, and means to reciprocate the strut in a proximaldistal direction.

16. The system of claim 14 wherein the means to see-saw the ultrasound transducer comprises a see-sawing stage upon which the ultrasound transducer is mounted, a reciprocating vertical strut bonded to one side of the stage, and a MEMS motor to reciprocate the strut in a proximal-distal direction.

17. The system of claim 14 wherein the means to see-saw the ultrasound transducer comprises a see-sawing stage upon which the ultrasound transducer is mounted, a reciprocating vertical strut bonded to one side of the stage, and a stationary vertical strut bonded to the opposite side of the stage, the stationary vertical strut and the reciprocating vertical strut each having a generally D-shaped cross-section, the stationary strut and reciprocating strut aligned with flat sides facing each other and curved portions facing away from each other, with the curved portions optionally fluted so as to allow passageways for fluid.

18. The system of claim 14 wherein the means to see-saw the ultrasound transducer comprises a see-sawing stage upon which the ultrasound transducer is mounted, a reciprocating vertical strut bonded to one side of the stage, a stationary vertical strut bonded to the opposite side of the stage, and a MEMS motor to drive the reciprocating strut in a proximal-distal direction.

19. The system of claim 18 wherein a channel is provided in the stationary vertical strut through which wires are threaded.

\* \* \* \* \*